(12) United States Patent
De Haan

(10) Patent No.: US 11,564,576 B2
(45) Date of Patent: Jan. 31, 2023

(54) DEVICE, SYSTEM AND METHOD FOR DETERMINING A TISSUE CHARACTERISTIC OF A SUBJECT

(71) Applicant: KONINKLIJKE PHILIPS N.V., Eindhoven (NL)

(72) Inventor: Gerard De Haan, Helmond (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 733 days.

(21) Appl. No.: 16/492,185

(22) PCT Filed: Mar. 7, 2018

(86) PCT No.: PCT/EP2018/055522
§ 371 (c)(1),
(2) Date: Sep. 9, 2019

(87) PCT Pub. No.: WO2018/166850
PCT Pub. Date: Sep. 20, 2018

(65) Prior Publication Data
US 2021/0137385 A1 May 13, 2021

(30) Foreign Application Priority Data
Mar. 13, 2017 (EP) ..................... 17160598

(51) Int. Cl.
*A61B 5/00* (2006.01)
*G16H 30/20* (2018.01)
(Continued)

(52) U.S. Cl.
CPC .......... *A61B 5/0051* (2013.01); *A61B 5/0077* (2013.01); *A61B 5/1075* (2013.01);
(Continued)

(58) Field of Classification Search
CPC ... A61B 5/7267; A61B 5/0077; A61B 5/1075; A61B 5/4875; A61B 5/4566;
(Continued)

(56) References Cited

U.S. PATENT DOCUMENTS

2003/0220556 A1 11/2003 Porat
2006/0058608 A1\* 3/2006 Hogan ............... A61B 5/14532
600/407
(Continued)

FOREIGN PATENT DOCUMENTS

| JP | 2013116419 A | 6/2013 |
|---|---|---|
| WO | 201340443 | 3/2013 |
| WO | 2014/004835 | 1/2014 |

OTHER PUBLICATIONS

International Search Report and Written Opinion dated May 22, 2018 for International Application No. PCT/EP2018/055522 Filed Mar. 7, 2018.
(Continued)

*Primary Examiner* — Pinalben Patel

(57) ABSTRACT

The present invention relates to a device, system and method for less obtrusively determining a tissue characteristic of a subject, the device comprises a first control unit (11) configured to control an electromechanical transducer (31) by a first control signal (21) to transfer mechanical waves varying in a frequency range or with varying frequency content to an exposed tissue area of the subject; a second control unit (12) configured to control an electromagnetic radiation emitter (32) by a second control signal (22) to emit electromagnetic radiation towards the exposed tissue area of the subject; a radiation signal input (13) configured to obtain a radiation signal (23) indicative of electromagnetic radiation reflected from the exposed tissue area of the subject; and a processor (14) configured to determine a tissue characteristic signal (24) indicative of a tissue characteristic of the exposed tissue
(Continued)

area of the subject derived from a frequency response or a frequency transfer function obtained from the obtained radiation signal in said frequency range or for said varying frequency content.

14 Claims, 1 Drawing Sheet

(51) Int. Cl.
 *G16H 50/20* (2018.01)
 *G16H 30/40* (2018.01)
 *A61B 5/107* (2006.01)

(52) U.S. Cl.
 CPC .............. *A61B 5/442* (2013.01); *A61B 5/444* (2013.01); *A61B 5/4566* (2013.01); *A61B 5/4872* (2013.01); *A61B 5/4875* (2013.01); *A61B 5/7267* (2013.01); *G16H 30/20* (2018.01); *G16H 30/40* (2018.01); *G16H 50/20* (2018.01); *A61B 2576/00* (2013.01)

(58) Field of Classification Search
 CPC ....... A61B 5/4872; A61B 5/444; A61B 5/442; A61B 5/0051; A61B 2576/00; A61B 5/0059; G16H 30/40; G16H 30/20; G16H 50/20; Y02A 90/10
 See application file for complete search history.

(56) References Cited

U.S. PATENT DOCUMENTS

| | | | |
|---|---|---|---|
| 2009/0245603 A1* | 10/2009 | Koruga | A61B 5/415 382/128 |
| 2009/0312644 A1 | 12/2009 | Kosugi | |
| 2013/0035569 A1 | 2/2013 | Heanue | |
| 2015/0148654 A1* | 5/2015 | Whanwook | A61B 5/0095 600/407 |
| 2016/0045115 A1 | 2/2016 | Chase | |
| 2016/0249849 A1 | 9/2016 | Mihara | |
| 2017/0181633 A1 | 6/2017 | Herrmann | |
| 2020/0337612 A1* | 10/2020 | Abul-Haj | A61B 5/0059 |

OTHER PUBLICATIONS

Kawchuk et al., "Structural health monitoring (vibration) as a tool for identifying structural alterations of the lumbar spine: a twin control study", Nature Scientific Reports, Mar. 11, 2016.
Moço, et al., "Ballistocardiographic Artifacts in PPG Imaging", IEEE, Tr. on Biomedical Engineering, vol. PP, No. 99, Nov. 2015.
Moço, et al., "Motion robust PPG-imaging through color channel mapping", Biomedical Optical Express, vol. 7, No. 5, pp. 1737-1754, May 2016.

* cited by examiner

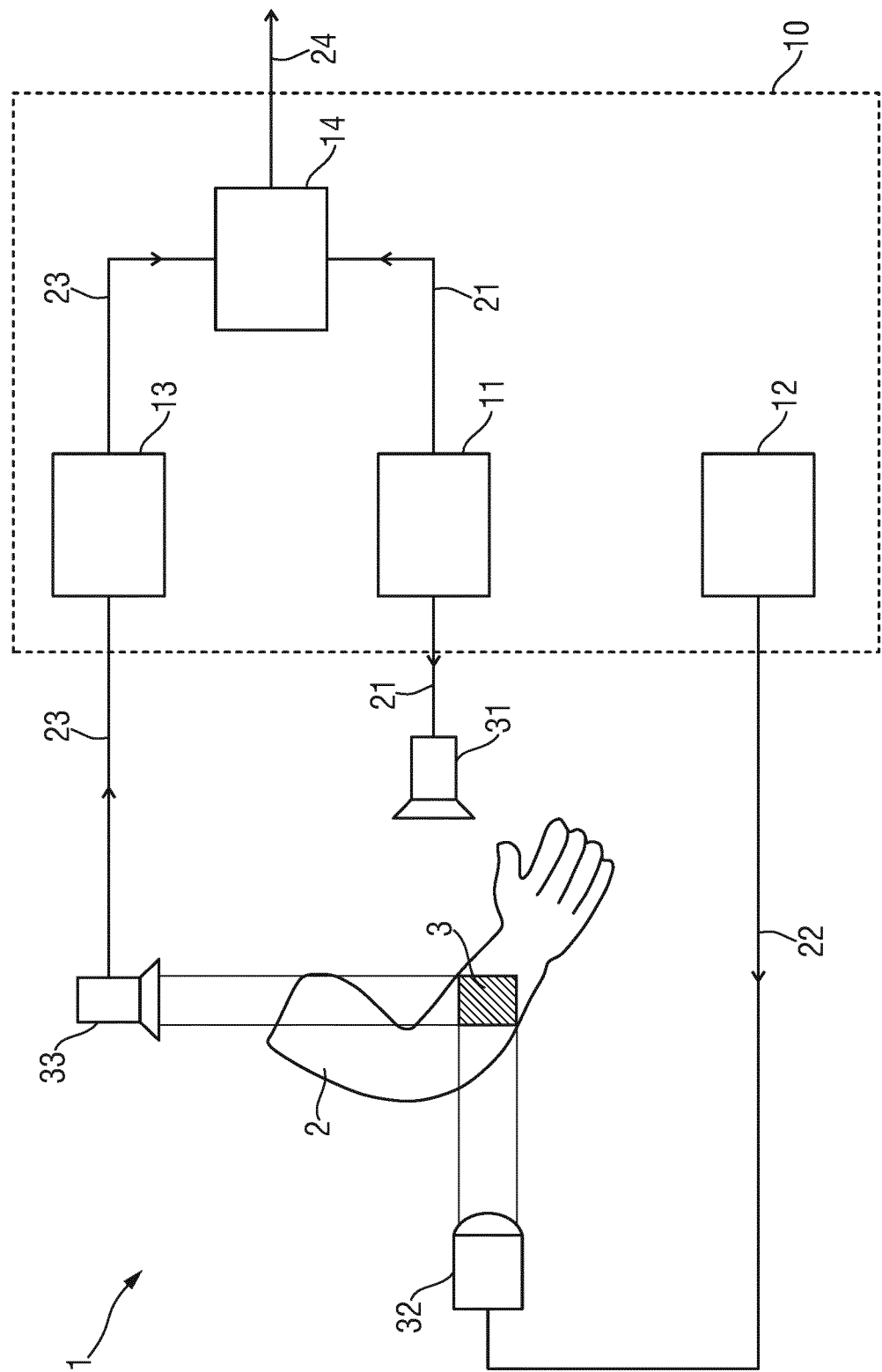

DEVICE, SYSTEM AND METHOD FOR DETERMINING A TISSUE CHARACTERISTIC OF A SUBJECT

CROSS REFERENCE TO RELATED APPLICATIONS

This application is the U.S. National Phase application under 35 U.S.C. § 371 of International Application No. PCT/EP2018/055522 filed Mar. 7, 2018, published as WO 2018/166850 on Sep. 20, 2018, which claims the benefit of European Patent Application Number 17160598.3 filed Mar. 13, 2017. These applications are hereby incorporated by reference herein.

FIELD OF THE INVENTION

The present invention relates to a device, system and method for determining a tissue characteristic of a subject.

BACKGROUND OF THE INVENTION

G. N. Kawchuk et al., "Structural health monitoring (vibration) as a tool for identifying structural alterations of the lumbar spine: a twin control study", Nature Scientific Reports, 11 Mar. 2016, shows how possible damage to the spine of a subject can be classified with mechanical means applying a vibration to the spine and measuring, with accelerometers, the frequency response of the spine. This method is, however, obtrusive and has limited applicability.

Hence, there is a need to provide a less obtrusive way of classifying possible damage to the spine of a subject, which may also have a broader applicability.

US 2016/0045115 A1 discloses a method for an optical elastography system that converts digital images of an actuated breast into a description of surface motion. The surface motion can subsequently be used to ascertain whether the breast has regions of abnormal stiffness, e.g., indicating a significant likelihood of breast cancer. The steps of the method use a model based segmentation to identify profile of the breast in each image, and for each pair of images computing skin surface motion using an optical flow algorithm. This method eliminates a preliminary step of placing fiducial markers on the subject.

SUMMARY OF THE INVENTION

It is an object of the present invention to provide a device, system and method for less obtrusively determining a tissue characteristic of a subject.

In a first aspect of the present invention a device for determining a tissue characteristic of a subject is presented comprising:

a first control unit configured to control an electromechanical transducer by a first control signal to transfer mechanical waves varying in a frequency range or with varying frequency content to an exposed tissue area of the subject;

a second control unit configured to control an electromagnetic radiation emitter by a second control signal to emit electromagnetic radiation towards the exposed tissue area of the subject;

a radiation signal input configured to obtain a radiation signal indicative of electromagnetic radiation reflected from the exposed tissue area of the subject; and a processor configured to determine a tissue characteristic signal indicative of a tissue characteristic of the exposed tissue area of the subject derived from a frequency response or a frequency transfer function obtained from the obtained radiation signal in said frequency range or for said varying frequency content.

In a further aspect of the present invention a system for determining a tissue characteristic of a subject is presented comprising:

an electromechanical transducer configured to transfer mechanical waves varying in a frequency range or with varying frequency content to an exposed tissue area of the subject;

an electromagnetic radiation emitter configured to emit electromagnetic radiation towards the exposed tissue area of the subject;

a radiation detector configured to detect electromagnetic radiation reflected from the exposed tissue area of the subject and to generate a radiation signal indicative of the detected electromagnetic radiation; and a device as disclosed herein for determining a tissue characteristic signal indicative of a tissue characteristic of the exposed tissue area of the subject derived from a frequency response or a frequency transfer function obtained from the radiation signal in said frequency range or for said varying frequency content.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device, in particular as defined in the dependent claims and as disclosed herein.

Recently, much progress has been achieved in the area of video health monitoring. Over the last decade, applications have emerged for respiration, pulse-rate, tissue perfusion-mapping, and SpO2 monitoring using regular video cameras (e.g. by use of remote photo-plethysmography, remote PPG), but also for sleep actigraphy, bed-entrance/leave, and other applications. While building knowledge in this developing field, and better understanding the limitations of camera-acquired data, new opportunities arise.

With the new knowledge obtained from research in video health monitoring, there are new opportunities, much broader applicable than the above cited publication of G. N. Kawchuk et al., and possibly fully non-obtrusive. It has particularly been recognized by the inventor that a camera would be a much more attractive means to acquire the various motion signals obtained according to the method described in the publication of G. N. Kawchuk et al. with a number of accelerometers attached to the subject's skin on top of the spine. Further, it is envisaged that also the motion signal may be obtained from the camera. This does also disturb the frequency response less, because of zero mass of the measurement system, and further prevent attachment of the various detectors at the skin, possible use of disposables, or cleaning between usages. The mechanical actuator may be replaced by a non-obtrusive actuator, while the application range can be much broader than just measuring spine health.

With the knowledge in the field of photo-plethysmography it is possible to discriminate between absorption induced color variation in living tissue due to cardiac activity (photoplethysmography, PPG), and motion-induced variations at the pulse-frequency (ballistocardiography, BCG). To arrive at viable options for camera-based motion measurement at the skin of a subject it is possible to use illumination of the skin. The camera (or, more generally, the radiation detector) allows replacing various accelerometers, by choosing a field of view that includes all necessary measurement sites. Further, in some applications the mechanical actuator may be replaced by an electromechanical transducer, e.g. a loudspeaker, enabling a totally unobtrusive measurement that can be applied for tissue characterization, e.g. for skin characterization, like measuring elasticity, possibly subcutaneous fat-layer quantification (fat thickness), hydration levels, detection of lesions, etc.

Thus, according to an aspect of the present invention an electromechanical transducer is used to provide a stimulus to a body part of a subject and an electromagnetic radiation sensor, e.g. a camera, and an electromagnetic radiation emitter, e.g. a light source, are used to measure a response of said body part. This response may be a frequency response, while different features may be extracted from a frequency transfer function (between input and output, possibly measured using a frequency sweep, or a set of signals with different frequency content) and a supervised learning algorithm can be used to build a classifier that, based on said features, and possibly features of the subject (age, gender, etc.) can provide the required tissue characteristic/health indicator.

According to an embodiment said processor is configured to determine the tissue characteristic signal by correlating the first control signal with the radiation signal or by combining (e.g. dividing) the frequency content of the radiation signal with the frequency content of the first control signal. For instance, a complex correlation may be used. This is particularly useful if the stimulus is a sinusoidal wave (with varying frequency). The complex correlation then involves taking the analytical signal from the stimulus signal, and correlating it with the radiation signal. The relative correlation for different frequencies of the sinusoidal stimulus provides directly the frequency transfer characteristic. In another embodiment, the frequency content of the radiation signal may be divided by the frequency content of the stimulus signal to obtain a frequency transfer function. This involves the use of a Fourier transform on both the stimulus and radiation signal.

The radiation signal input may be configured to obtain a plurality of radiation signals including a radiation signal per pixel or group of pixels within the exposed tissue area of the subject, wherein said processor is configured to determine the tissue characteristic signal by correlating the AC variations of the first control signal with the AC variations of a mean pixel value, in particular a time-normalized mean pixel value, over a group of pixels corresponding to at least part of the exposed tissue area of the subject, said AC variation being derived from said radiation signals. For instance, from the images obtained by a camera the mean pixel value of multiple groups of pixels can be determined. Each of these means can be traced over time, resulting in a signal for said group of pixels. These signals can then be divided by their mean to obtain normalized signals, from which the AC signals (AC variations) are obtained by subtracting. With this embodiment reasonable result can be achieved with limited processing efforts.

In another embodiment said processor is configured to determine the tissue characteristic signal by use of a classifier that uses features of the radiation signal, of the tissue characteristic signal, of the subject and/or of the tissue-location and/or that has been trained on tissues from subjects with different tissue characteristics. Features used by the classifier may e.g. include the frequency response, e.g. the response-peak (frequency with the highest gain), or the area under the curve of the frequency response. Other features are features of the subject, such as age, weight and gender. The use of a classifier improves the determination of some tissue characteristics.

The first control unit may be configured to control the electromechanical transducer to transfer mechanical waves varying in a frequency range between 1 Hz and 5000 Hz, in particular between 10 Hz and 1000 Hz, or with varying frequency content. The range will also determine whether a loudspeaker is feasible, or another electromechanical transducer (e.g. with direct contact, as in the Nature paper) may be preferred. This may limit the lower frequency spectrum. With respect to the upper limit the electromagnetic radiation emitter is of interest, particularly if it is a 2D sensor array (imager). Without sub-sampling it is likely that a camera will sacrifice resolution with higher picture-rates (binning of pixels). With sub-sampling this can likely be extended orders of magnitude, using the same principle as a sequential equivalent-time sampling oscilloscope (often simply referred to as a sampling oscilloscope). In this case the sampling in some embodiments may be controlled by the electromagnetic radiation emitter (e.g. flashing LEDs, during a longer integration period of the camera).

The second control unit may be configured to control the electromagnetic radiation emitter to emit electromagnetic radiation in a wavelength range between 300 nm and 1000 nm, in particular between 600 nm and 700 nm or between 400 nm and 500 nm. For silicon optical sensors the widest range is likely between 300 nm and 1000 nm. Red light (around 650 nm) may be particularly interesting because it gives a high sensor sensitivity and a very low pollution from PPG signals. On the other hand, the skin is translucent for red light which limits the spatial resolution. A much shorter wavelength, e.g. blue light 450 nm would likely give a better spatial resolution, while the penetration depth into the tissue is so small that little effect on the absorption from varying blood volumes during the cardiac cycle may be observed.

In a particular application said processor is configured to determine the tissue characteristic signal related to the subject's spine health, in particular by providing a quantification of possible damage to the spine.

In other applications said processor is configured to determine the tissue characteristic signal related to the subject's skin, in particular the elasticity, or related to one or more characteristics derived from the tissue characteristic signal related to the subject's skin, in particular sub-cutaneous fat thickness or hydration status.

To further improve the determination of the tissue characteristic, said radiation signal input is configured to obtain two or more radiation signals indicative of electromagnetic radiation reflected from two or more different exposed tissue areas of the subject and said processor is configured to determine the tissue characteristic signal per radiation signal and to combine the determined tissue characteristic signals into a combined tissue characteristic signal. For instance the average or weighted average of the determined tissue characteristic signals may be formed to increase the reliability of the obtained result.

Various components can be used to implement the components of the disclosed system. The electromechanical transducer may comprise a sound emitter, in particular a loudspeaker. The electromagnetic radiation emitter may comprise a light source, in particular an LED. The radiation detector may comprise a single photo-sensor, e.g. photodiode, with or without optical lens, or an imaging unit, in particular a video camera. Preferably, components are used that are not in contact with the subject's tissue during operation. Some or all of the components may be integrated into a common device, but may also be used as separate devices.

In a particularly preferred embodiment the electromagnetic radiation emitter is configured to emit the light under an oblique angle towards the exposed tissue area of the subject, which further improves the detection, since small tissue movements then more strongly modulate the reflected light. It should be noted that it is not impossible to use ambient light instead of electromagnetic radiation emitted by a dedicated electromagnetic radiation emitter. However, it is highly advantageous to use electromagnetic radiation, in particular light under an oblique angle, because the sensitivity for motion is much higher then, while it further helps to use red or blue light, since this reduces the pollution by absorption variations due to cardiac activity (PPG signal from the tissue, is weakest in red light of approximately 650 nm).

In critical applications, it may further be advantageous to use polarized light and a polarizer in the optical path of the detector, to focus on specularly reflected light and reduce the influence of diffusely reflected light from the tissue (which may be modulated by PPG).

BRIEF DESCRIPTION OF THE DRAWINGS

These and other aspects of the invention will be apparent from and elucidated with reference to the embodiment(s) described hereinafter. In the following drawings FIG. 1 shows a schematic diagram of a system and a device according to the present invention.

DETAILED DESCRIPTION OF EMBODIMENTS

FIG. 1 shows a schematic diagram of a system 1 and a device 10 determining a tissue characteristic of a subject (represented by the subject's arm 2) according to the present invention.

The system 1 comprises an electromechanical transducer 31, e.g. a loudspeaker, configured to transfer mechanical waves, e.g. acoustical waves transmitted through the air to the tissue of the subject, varying in a frequency range (i.e. a frequency sweep) or with varying frequency content to an exposed tissue area of the subject, in this embodiment an area 3 of a person's arm 2. The system 1 further comprises an electromagnetic radiation emitter 32, e.g. a light source such as an LED, configured to emit electromagnetic radiation 22 towards the exposed tissue area 3 of the subject. By use of a radiation detector 33, e.g. an optical sensor such as a video camera, electromagnetic radiation reflected from the exposed tissue area 3 of the subject is detected and a radiation signal 23 indicative of the detected electromagnetic radiation is generated. The device 10 determines a tissue characteristic signal 24 indicative of a tissue characteristic of the exposed tissue area 3 of the subject from the radiation signal 23 in said frequency range.

The device 10 comprises a first control unit 11 configured to control an electromechanical transducer 31 by a first control signal 21 to transfer mechanical waves varying in a frequency range or with varying frequency content to an exposed tissue area of the subject and a second control unit 12 configured to control an electromagnetic radiation emitter 32 by a second control signal 22 to emit electromagnetic radiation towards the exposed tissue area of the subject. The first and second control units 11, 12 may be control outputs of a controller or a control signal interface to which the electromechanical transducer 31 and the electromagnetic radiation emitter 32 are coupled.

The device 10 further comprises a radiation signal input 13 configured to obtain a radiation signal 23 indicative of electromagnetic radiation reflected from the exposed tissue area of the subject. The radiation signal input may be a signal interface to which the radiation detector 33 is coupled. By use of a processor 14 a tissue characteristic signal 24 indicative of a tissue characteristic of the exposed tissue area of the subject derived from the obtained radiation signal in said frequency range is determined.

The elements of the system 1 may be separate devices or may be partly or completely integrated into a common device. The device 10 may be implemented in soft- and/or hardware, e.g. as software application running on a computer, processor, electronic user device, etc.

In an embodiment for determining the tissue characteristic signal 24 it shall be assumed that the first control signal 21 (and thus the mechanical waves controlled by it) is a sinusoid of time-varying frequency. The radiation signal 23 then also can be expected to show a sinusoidal component with the same frequency because the vibration of the tissue surface causes a light modulation, and likely a different phase and amplitude. If an analytic signal is constructed from the first control signal 21 (e.g. using Hilbert Transform), an amplitude and phase of the radiation signal 23 (preferably after time-normalization, i.e. AC/DC) can be computed. This represents an example of a correlation, i.e. in this embodiment the normalized AC variation signal from the radiation signal 23 is correlated (inner product of time samples) with the unity-amplitude analytical signal of the first control signal 21. This resembles the procedure to build an amplitude and phase map from the BCG-signals as described e.g. in A. Moço, S. Stuijk, and G. de Haan, "Ballistocardiographic Artifacts in PPG Imaging", IEEE, Tr. on Biomedical Engineering, Vol. PP, No. 99, November 2015.

After sweeping through a frequency range, while keeping the amplitude of the first control signal 21 constant, a frequency characteristic (both amplitude and phase) is obtained. Instead of keeping the amplitude constant, it is also possible to divide the output (from the radiation signal 23) by the input (the first control signal 21) amplitude. The obtained frequency characteristic is the tissue characteristic signal 24.

Further characteristics may be determined from this frequency response, e.g. the response peak (frequency with the highest gain), or the area under the curve of the frequency response.

Rather than a frequency sweep, pulse trains with different frequency content may be applied. In this case the frequency response may be derived from the relative strength of the frequencies in each pulse train.

The peak frequency response, when measuring e.g. from skin tissue, contains information about the skin health. Aging is known to reduce collagen, and it is reasonable that this shows in the frequency response (the stiffer the skin, the higher the peak response frequency). Also the thickness of the sub-cutaneous fat-layer modifies the response, and finally also hydration levels affect the response.

Depending on the excitation frequencies, the radiation sensor 33, particularly if it is a camera, may not be able to sample at a rate high enough to resolve all frequencies in the first control signal 21. In this case the frequency response can only be determined by computing the response from multiple registrations of the same input waveform. This is in analogy with a sampling oscilloscope that can also show periodic signals well above its sampling frequency.

In a preferred embodiment the radiation emitter 32 is a light source that emits the light under an oblique angle towards the subject's tissue in order to maximize the light modulation caused by vibrating tissue.

The acoustical waves are preferably in a frequency range between 1 Hz and 5000 Hz and the electromagnetic radiation preferably includes an emission in the range 300-1000 nm, particularly having a peak emission at approximately 660 nm, i.e. the absorption dip of blood, or below 475 nm where the penetration of light into skin is low due to scattering.

The output tissue characteristic may be related to the subject's spine health, e.g. providing a quantification of possible damage to the spine. In other applications the tissue characteristic is related to the subject's skin, or internal organs, e.g. the elasticity, or derived characteristics like sub-cutaneous fat thickness, or hydration status.

The characteristic may be measured at different body tissue sites, simultaneously or sequentially, and the individual characteristics may be combined into a combined tissue characteristic to increase accuracy and reliability.

The frequency transfer is determined in an embodiment by correlating the input signal to the electromechanical emitter 31 with the output AC variations of the mean pixel value over a group of pixels corresponding with a tissue region 3 of the subject. More specifically, a complex correlation can be useful, where the Hilbert Transform is used to get the analytic signal from the input frequency sweep (i.e. the control signal 21), and this analytic signal is correlated with the output signal 23 obtained from the radiation detector 33.

In a practical embodiment, the tissue characteristic results from a classifier (employed by the processor 14) that uses features of the frequency response/transfer and has preferably been trained on tissues from subjects with different tissue characteristics.

Characteristics of the frequency response, e.g. the response peak (frequency with the highest gain), or the area under the curve of the frequency response can be examples of the features used in a classifier. In addition, the age, gender of the person, and tissue location (arm, cheek, etc.) may be additional features to determine health parameters of the skin, as the characteristics are expected to shift with age and depend on gender. For example, if the hydration levels shall be estimated, age and gender may be used as known features to improve the estimate.

The invention can preferably be used in spine and skin health diagnosis.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for determining a tissue characteristic of a subject, said device comprising:
    a first controller configured to control an electromechanical transducer by a first control signal to transfer mechanical waves varying in a frequency range or with varying frequency content to an exposed tissue area of the subject, wherein said first controller is configured to control the electromechanical transducer to transfer mechanical waves varying in a frequency range between 1 Hz and 5000 Hz, optionally between 10 Hz and 1000 Hz;
    a second controller configured to control an electromagnetic radiation emitter by a second control signal to emit electromagnetic radiation towards the exposed tissue area of the subject;
    a radiation signal input configured to obtain a radiation signal indicative of electromagnetic radiation reflected from the exposed tissue area of the subject; and
    a processor configured to determine a tissue characteristic signal indicative of a tissue characteristic of the exposed tissue area of the subject derived from a frequency response or a frequency transfer function obtained from the obtained radiation signal in said frequency range or for said varying frequency content.

2. The device as claimed in claim 1,
    wherein said processor is configured to determine the tissue characteristic signal by correlating the first control signal with the radiation signal or by combining the frequency content of the radiation signal with the frequency content of the first control signal.

3. The device as claimed in claim 2,
    wherein said radiation signal input is configured to obtain a plurality of radiation signals including a radiation signal per pixel or group of pixels within the exposed tissue area of the subject and
    wherein said processor is configured to determine the tissue characteristic signal by correlating the AC variations of the first control signal with the AC variations of a mean pixel value, optionally a time-normalized mean pixel value, over a group of pixels corresponding to at least part of the exposed tissue area of the subject, said AC variation being derived from said radiation signals.

4. The device as claimed in claim 1,
    wherein said processor is configured to determine the tissue characteristic signal by use of a classifier that uses features of the radiation signal, of the tissue characteristic signal, of the subject and/or of the tissue-location.

5. The device as claimed in claim 1,
wherein said processor is configured to determine the tissue characteristic signal by use of a classifier that and/or that has been trained on tissues from subjects with different tissue characteristics.

6. The device as claimed in claim 1,
wherein said processor is configured to determine the tissue characteristic signal related to the subject's spine health, optionally by providing a quantification of possible damage to the spine.

7. The device as claimed in claim 1,
wherein said processor is configured to determine the tissue characteristic signal related to the subject's skin, optionally the elasticity, or related to one or more characteristics derived from the tissue characteristic signal related to the subject's skin, optionally elasticity, sub-cutaneous fat thickness, lesions, or hydration status.

8. The device as claimed in claim 1,
wherein said radiation signal input is configured to obtain two or more radiation signals indicative of electromagnetic radiation reflected from two or more different exposed tissue areas of the subject and
wherein said processor is configured to determine the tissue characteristic signal per radiation signal and to combine the determined tissue characteristic signals into a combined tissue characteristic signal.

9. A system for determining a tissue characteristic of a subject, said system comprising:
an electromechanical transducer configured to transfer mechanical waves varying in a frequency range or with varying frequency content to an exposed tissue area of the subject;
an electromagnetic radiation emitter configured to emit electromagnetic radiation towards the exposed tissue area of the subject;
a radiation detector configured to detect electromagnetic radiation reflected from the exposed tissue area of the subject and to generate a radiation signal indicative of the detected electromagnetic radiation; and
a device as claimed in claim 1 for determining a tissue characteristic signal indicative of a tissue characteristic of the exposed tissue area of the subject derived from a frequency response or a frequency transfer function obtained from the radiation signal in said frequency range or for said varying frequency content.

10. The system as claimed in claim 9,
wherein said electromechanical transducer comprises a sound emitter, optionally a loudspeaker, and/or
wherein said electromagnetic radiation emitter comprises a light source, optionally an LED, and/or
wherein said radiation detector comprises an imaging unit, optionally a video camera.

11. The system as claimed in claim 9,
wherein said electromagnetic radiation emitter is configured to emit the light under an oblique angle towards the exposed tissue area of the subject.

12. A device for determining a tissue characteristic of a subject, said device comprising:
a first controller configured to control an electromechanical transducer by a first control signal to transfer mechanical waves varying in a frequency range or with varying frequency content to an exposed tissue area of the subject;
a second controller configured to control an electromagnetic radiation emitter by a second control signal to emit electromagnetic radiation towards the exposed tissue area of the subject, wherein said second controller is configured to control the electromagnetic radiation emitter to emit electromagnetic radiation in a wavelength range between 300 nm and 1000 nm, optionally between 600 nm and 700 nm or between 400 nm and 500 nm;
a radiation signal input configured to obtain a radiation signal indicative of electromagnetic radiation reflected from the exposed tissue area of the subject; and
a processor configured to determine a tissue characteristic signal indicative of a tissue characteristic of the exposed tissue area of the subject derived from a frequency response or a frequency transfer function obtained from the obtained radiation signal in said frequency range or for said varying frequency content.

13. A method for determining a tissue characteristic of a subject, said method comprising:
controlling an electromechanical transducer by a first control signal to transfer mechanical waves varying in a frequency range or with varying frequency content to an exposed tissue area of the subject, wherein the frequency range is between 1 Hz and 5000 Hz, optionally between 10 Hz and 1000 Hz;
controlling an electromagnetic radiation emitter by a second control signal to emit electromagnetic radiation towards the exposed tissue area of the subject;
obtaining a radiation signal indicative of electromagnetic radiation reflected from the exposed tissue area of the subject; and
determining a tissue characteristic signal indicative of a tissue characteristic of the exposed tissue area of the subject derived from a frequency response or a frequency transfer function obtained from the obtained radiation signal in said frequency range or for said varying frequency content.

14. A computer program stored on a non-transitory computer-readable medium, comprising program code means for causing a computer to carry out the steps of the method as claimed in claim 13 when said computer program is carried out on the computer.

* * * * *